US011684792B2

(12) United States Patent
Guiney et al.

(10) Patent No.: US 11,684,792 B2
(45) Date of Patent: Jun. 27, 2023

(54) MONITOR DEFIBRILLATOR WITH TOUCH SCREEN U/I FOR ECG REVIEW AND THERAPY

(71) Applicant: KONINKLIJKE PHILIPS N.V., Eindhoven (NL)

(72) Inventors: Patrick Guiney, Concord, MA (US); William Douglas Grube, Windham, NH (US); John Mardirosian, Westford, MA (US); Scott Alan Wuthrich, Reading, MA (US); Simon Edward Kozin, Medford, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/776,793

(22) PCT Filed: Mar. 14, 2014

(86) PCT No.: PCT/IB2014/059785
§ 371 (c)(1),
(2) Date: Sep. 15, 2015

(87) PCT Pub. No.: WO2014/141167
PCT Pub. Date: Sep. 18, 2014

(65) Prior Publication Data
US 2016/0030758 A1    Feb. 4, 2016

Related U.S. Application Data

(60) Provisional application No. 61/789,248, filed on Mar. 15, 2013.

(51) Int. Cl.
*A61N 1/39* (2006.01)

(52) U.S. Cl.
CPC ......... *A61N 1/3993* (2013.01); *A61N 1/3925* (2013.01)

(58) Field of Classification Search
CPC ........................... A61N 1/3925; A61N 1/3993
See application file for complete search history.

(56) References Cited

U.S. PATENT DOCUMENTS 6,321,113 B1 * 11/2001 Parker .................... G16H 40/63
607/5
6,463,320 B1 * 10/2002 Xue ....................... A61B 5/7475
600/523

(Continued)

FOREIGN PATENT DOCUMENTS

CN          201098465 Y      8/2008
JP          H11216119 A      8/1999

(Continued)

*Primary Examiner* — Mallika D Fairchild (57) ABSTRACT

A device (200) which includes a monitoring unit (210), a therapy unit (220), and a display (100) that includes a touch screen (110). The monitoring unit (210) can be configured to monitor a person's vital signs, such as a person's electrocardiogram (ECG). The therapy unit (220) can be configured to administer an electric shock. The display (100) can be configured to display the ECG and enable a user to scroll the displayed ECG back and forth and/or to zoom in and zoom out the displayed ECG by touching the touch screen (110). The display (100) can also be configured to enable the user to select two or more separate segments of the ECG to view together at the same time on the display (100), which segments can be separated by intervening segments of the ECG that can be hidden from being viewed on the display (100). The display (100) can have multiple user-interface windows (120, 130). One window (120) can be configured to only display functions related to the monitor unit (210) and/or the therapy unit (220), while another window (130)

(Continued)

can be configured to display software applications, including an electronic patient care record (ePCR) application.

18 Claims, 4 Drawing Sheets

(56) References Cited

U.S. PATENT DOCUMENTS

| | | | |
|---|---|---|---|
| 6,898,462 B2 | 5/2005 | Rock et al. | |
| 8,038,617 B2 | 10/2011 | Maschke | |
| 2002/0105504 A1* | 8/2002 | Toepke | G06F 3/04886 345/173 |
| 2003/0028219 A1* | 2/2003 | Powers | A61N 1/39 607/5 |
| 2003/0088284 A1* | 5/2003 | Daynes | A61N 1/39 607/5 |
| 2004/0122476 A1* | 6/2004 | Wung | A61B 5/044 607/5 |
| 2004/0204743 A1* | 10/2004 | McGrath | A61N 1/08 607/5 |
| 2006/0058848 A1* | 3/2006 | Piraino | A61N 1/3993 607/5 |
| 2008/0004663 A1* | 1/2008 | Jorgenson | A61N 1/37247 607/5 |
| 2009/0259960 A1 | 10/2009 | Steinle et al. | |
| 2011/0213262 A1* | 9/2011 | Vaisnys | A61N 1/3904 600/523 |
| 2011/0214055 A1 | 9/2011 | Georgiev et al. | |
| 2011/0246875 A1* | 10/2011 | Parker | G06F 3/04845 715/702 |
| 2012/0123223 A1 | 5/2012 | Freeman et al. | |
| 2014/0019901 A1* | 1/2014 | Powell | A61B 5/0006 715/771 |
| 2016/0030758 A1 | 2/2016 | Guiney et al. | |

FOREIGN PATENT DOCUMENTS

| | | |
|---|---|---|
| JP | 2005524498 A | 8/2005 |
| JP | 2013518676 A | 5/2013 |
| JP | 2013524371 A | 6/2013 |
| JP | 2014503235 A | 2/2014 |
| WO | 2011097312 A1 | 8/2011 |
| WO | 2011106185 A1 | 9/2011 |
| WO | 2011127459 A1 | 10/2011 |
| WO | 2012065131 A1 | 5/2012 |
| WO | 2012099933 A2 | 7/2012 |
| WO | 2014102726 A1 | 7/2014 |

* cited by examiner

MONITOR DEFIBRILLATOR WITH TOUCH SCREEN U/I FOR ECG REVIEW AND THERAPY

CROSS-REFERENCE TO PRIOR APPLICATIONS

This application is the U.S. National Phase application under 35 U.S.C. § 371 of International Application No. PCT/IB14/059785, filed on Mar. 14, 2014, which claims the benefit of U.S. Provisional Patent Application No. 61/789,248, filed on Mar. 15, 2013. These applications are hereby incorporated by reference herein.

The present disclosure relates to, e.g., medical devices and systems, and more particularly to novel and inventive monitor defibrillators with a touch screen user interface for electrocardiogram (ECG) review and therapy, and monitor defibrillators having a touchscreen with additional user interface window(s).

Currently, monitor defibrillators are not known to be available with touch screen displays. There are many reasons for this, including, e.g., that users of monitor defibrillators often wear rubber gloves (sometimes two pairs of rubber gloves). Common touch screen technologies generally do not work properly if the user is wearing rubber gloves, especially when the gloves prevent the user's fingers from sliding smoothly across display's glass surface, for example. Additionally, device displays are sometimes exposed to rain and other fluids. Common touch screen technologies do not work properly when fluid droplets are present on display's glass surface, especially if the fluid is electrically conductive, which it is typically.

Thus, although touch screens are currently not known to be available on monitor defibrillators for such reasons, touch screen displays are available and used in many tablet computers and smart phones that are currently available. Typically, users utilize the touch screens built into these products to interact with them in the following two ways:

1) Single-Touch Controls: E.g., menus and soft keys are activated using a single touch by the user on the touch screen.

2) Multi-Touch Controls: E.g., zooming, paging, scrolling, and other display navigation functions are accomplished by having the user "pinch and expand" or "touch and swipe" the touch screen.

The present disclosure discloses and describes, e.g., monitors defibrillators having a touch screen user interface that can have both single-touch and multi-touch controls. In addition to the touch screen user interface providing functions and applications of a graphical user interface utilizing touch screen technology similar to what is already found on tablet computers and smart phones, additional functions and applications are provided that are unique to monitors and defibrillators. Moreover, by employing a touch screen user interface, such additional functions and applications that are unique to monitors and defibrillators can be provided in a revolutionary manner, providing a user with functionality and capabilities that goes beyond that which is currently known to be available on monitors and defibrillators.

Currently available monitor defibrillators generally have several user interface issues/problems that touch screen technology can overcome, including:

Entering detailed patient information is currently difficult and time consuming. Full keyboards are too big and bulky to be considered practical for monitor defibrillators. Softkey buttons and rotary click wheels require the user to scroll through many options before finding the right character.

Touch screen technology can allow on-screen keypads to be available (e.g., pop up) when needed, making detailed patient information much easier and quick to enter.

Menu structures are generally complicated and difficult to use. Users typically currently have to use multiple button presses to access important functions (e.g., press menu, navigate using up/down keys, and then hit select).

Touch screen technology can allow much easier access to functions. Users can simply touch a desired menu, slide their finger to the needed function, and then select it by lifting their finger off the display.

Zooming, paging, and other display navigation functions are currently difficult to implement. For example, changing the amplitude of the ECG waveform requires either dedicated up/down hard keys, or a multiple step selection process using menu and soft keys.

Touch screen technology can allow the user to simply touch the waveform and enlarge it by pinching out (e.g., via multi-touch implementation).

Review of ECG waveforms on the display of a monitor defibrillator is generally currently limited to short segments of several seconds even though device memory may record hours of data from one patient. To review longer segments of recorded ECG typically requires printing to a small strip chart printer. The small printers in monitor defibrillators are typically slow and prone to mechanical failure, especially when subjected to drop shock, vibration and other hazards. Use of mechanical controls (function buttons, membrane keypads, scroll wheels, etc.) to review extended ECG data in memory is generally considered to be not convenient or intuitive. Mechanical controls are largely physically separate from the displayed ECG and require operator actuations to select and scroll through an ECG waveform of interest.

Use of mechanical controls (e.g., function buttons, membrane keypads, scroll wheels, etc.) to manipulate displayed ECG waveforms is generally not convenient or intuitive. Mechanical controls are largely physically separate from the displayed ECG and require operator actuations to select a waveform of interest and a desired action to enlarge or contract the waveform.

It is believed that all existing monitor defibrillators employ mechanical controls to select energy level, charge, shock and synchronize patient therapy. Mechanical controls for therapy typically include rotary switches, scroll wheels, buttons, membrane switches and other electro-mechanical input devices. Mechanical input devices with moving components are typically less reliable than electronic input devices with no moving components. In order to accommodate a wide variety of hand sizes, mechanical controls for therapy are also typically large and consume substantial space on the monitor defibrillator control panel.

Additionally, the touch screen will eliminate or reduce the need for localization of some labels and it allows the customization of device features without changing mechanical components (e.g., changing the max therapy setting, adding pacing, etc.).

The present invention provides for overcoming these and other issues/problems in addition to enabling new functionality not possible with existing user interfaces of monitors defibrillators.

In accordance with an exemplary embodiment of the present invention, provided is a device which includes a monitoring unit, a therapy unit, and a display that includes a touch screen.

The monitoring unit can be configured to monitor a person's vital signs, such as a person's electrocardiogram (ECG). The display can be configured to display the ECG.

Further, the display can be configured to enable a user to scroll the displayed ECG back and forth by touching the touch screen. The display can be configured to also enable a user to zoom in and zoom out the displayed ECG by touching the touch screen.

In addition, the display can be configured to enable a user to select two or more separate segments of the ECG to view together at the same time on the display. The segments can be separated by intervening segments of the ECG, and the display can be configured to enable the user to hide the intervening segments from being viewed on the display.

The touch screen can be configured to be used by the user via single-touch controls and/or multi-touch controls.

The display can be configured to have multiple user-interface windows. One window can be configured to only display functions related to the monitor unit and/or the therapy unit. One or more windows can be configured to display one or more software applications, which software applications can include an electronic patient care record (ePCR) application.

The therapy unit can be configured to administer an electric shock.

The touch screen can be configured to enable a user to set monitoring parameters, initiate the administration of the electric shock, navigate menus, enter information in the ePCR, and/or retrieve and/or transmit information to a remote computer and/or the cloud.

In accordance with another exemplary embodiment of the present invention, a method of manufacturing a device is provided, the exemplary method including providing a monitoring unit, providing a therapy unit, and providing a display unit having a touch screen, where the touch screen is configured so that a person can use at least one of single-touch or multi-touch gestures to display information from the monitoring unit, including controlling what information from the monitoring unit is displayed and how the information from the monitoring unit is displayed, and to control the therapy unit.

The exemplary method can further include configuring the monitoring unit to be capable of monitor a person's electrocardiogram (ECG). The exemplary method can also further include configuring the therapy unit to be capable of administering an electric shock.

In accordance with yet another exemplary embodiment of the present invention, provided is a method of using a device including a monitoring unit, a therapy unit, and a display unit having a touch screen. The method includes using single-touch and/or multi-touch gestures to display information from the monitoring unit, including controlling what information from the monitoring unit is displayed and how the information from the monitoring unit is displayed; and using single-touch and/or multi-touch gestures to control the therapy unit.

The exemplary method can further include monitoring a person's electrocardiogram (ECG) displayed on the display unit and administering an electric shock via the therapy unit based on information displayed on the display unit.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

To facilitate an understanding of the present invention, exemplary embodiments of the present invention are described herein with reference to the accompanying figures.

For example, in addition to the solutions and advantages provided above in connection with specific issues/problems, exemplary embodiments of a monitor defibrillator according to the present invention disclosed and described herein can have a graphical user interface that utilizes touch screen technology to provide one or more (or all) of the following important features/functionality:

Easy to use (e.g., intuitive user controls);

Quick access to important controls (e.g., focused controls based on how device is being used);

Easy selection of function menus and soft keys (e.g., using single-touch functionality);

More powerful and interactive display navigation functions (e.g., using multi-touch functionality);

Fewer dedicated hard keys and labels (e.g., less cluttered and expensive, simple to translate).

According to exemplary embodiments of the present invention, the graphical user interface utilizing touch screen technology can be implemented with single-touch and/or multi-touch controls. This can be accomplished by utilizing/implementing the following touch screen technologies, for example:

Resistive touch (both analogue and digital); and/or

Projected capacitive touch.

These particular touch technologies can be preferred for use in monitors defibrillators based on their ability to work for users wearing rubber gloves and their reliability in harsh environments (e.g., outdoor use where displays may get wet).

Further, touch screen technologies are constantly being refined and improved (e.g., increased resolution and lower cost). It is contemplated that such refined and improved touch screen technologies are included within the scope of the present invention.

In addition to the functionality and benefits described above, exemplary embodiments of the present invention can provide for additional functionality and applications which are unique to monitor defibrillators, including some of which can be provided in a revolutionary manner, providing a user with functionality and capabilities that goes beyond that which is currently known to be available with monitors and defibrillators. For example, exemplary embodiments of the present invention can provide for:

Use of touch screen to select and review extended ECG waveform;

Use of touch screen to select and manipulate displayed ECG waveform; and

Use of touch screen to replace mechanical controls for therapy.

For example, according to exemplary embodiments of the present invention, use of touch screen is provided to select and review extended ECG waveform. For example, with a touch screen user interface, an operator places one finger directly on the screen to review the displayed ECG waveform of interest. Gestures such as sliding one finger to the left or right advance the displayed portion of the waveform backward or forward, respectively, through recorded ECG memory. Slow gestures provide fine temporal resolution (seconds) while more rapid gestures allow operators to quickly scan through extended ECG memory (minutes & hours). Directly touching the displayed waveform is intuitive and eliminates the need for extra actions via mechanical controls to select a waveform of interest and the desired action to review the waveform.

Exemplary embodiments of the present invention can (also) provide for use of gestures to select and manipulate (e.g., expand or contract) displayed ECG waveform. For example, with a touch screen user interface, an operator places two fingers directly on the screen to manipulate a displayed ECG waveform of interest. By using two fingers, an operator applies pinching gestures (bringing fingertips closer together or farther apart) to the touch screen in order to expand or contract the graphic display of the ECG waveform. As provided above, directly touching the displayed waveform would generally be considered intuitive and eliminate the need for extra actions via mechanical controls to select a waveform of interest and desired action to manipulate the waveform.

Exemplary embodiments of the present invention can (also) provide for use of touch screen to replace mechanical controls for therapy. For example, on the touch screen user interface, graphic icons for therapy controls replace the traditional mechanical controls. An operator momentarily touches graphic icons for Charge, Shock, Synchronize or Pacing instead of momentarily pressing a mechanical switch to activate the corresponding function. For energy selection, the touch screen user interface displays a list of energy levels and prompts the operator to touch the desired energy level. Alternatively, the touch screen user interface displays one energy level and provides two or more additional control icons to increase or decrease the energy level selection.

Further, exemplary embodiments of a monitor defibrillator according to the present invention can be provided with a touchscreen for additional user interface window(s). For example, a single touchscreen implemented on a monitor defibrillator in accordance with exemplary embodiments of the present invention can provide a graphical user interface for both the monitor defibrillator and an independent software application such as an electronic patient care records (ePCR) application.

Under current practice with currently available technology, EMS personnel typically obtain and manage patient clinical information using monitor defibrillators and other software such as 3rd party applications for the electronic patient care record (ePCR). The monitor defibrillator has one user interface while other software applications generally require a separate user interface on a laptop or other computer or tablet. Accordingly, EMS personnel must typically juggle two devices and two or more user interfaces to collect and manage information when treating patients. This current practice with currently available technology can cause numerous disadvantages and potentially serious problems, including, e.g., redundant entry of information, increased likelihood of data entry errors, and time away from often vital and time critical clinical diagnostic and/or treatment) activities.

Exemplary embodiments according to the present invention can solve these and other issues/problems. For example:

Eliminate duplicate hardware: With connectivity and cloud computing, there is a diminishing need for dedicated computer hardware to run software applications apart from a user interface. Exemplary embodiments according to the present invention of a monitor defibrillator system with a touchscreen that supports multiple user interfaces can eliminate the need and extra expense for dedicated laptops or other computers or tablets to run independent or third-party software applications.

Vital signs can be always visible in medic's field of view: With separate user interface hardware, a medic typically must look away from the monitor defibrillator interface to operate and interact with independent or third-party software applications such as an ePCR running on a separate laptop or other computer or tablet. In accordance with exemplary embodiments of the present invention, multiple user interfaces can be integrated on one monitor defibrillator touchscreen allowing the medic to remain focused and aware of the patient vital signs by providing a continuous display of this information in their immediate field of view even while interfacing with an ePCR, since the ePCR is provided on the same touch screen (e.g., in a separate user-interface window or section of the touch screen).

Simplifies data transfer: The typical process of sending data from one device or software application to another in the EMS environment is typically complex, requiring multiple steps at the user interfaces of both the origin and destination. In accordance with exemplary embodiments of the present invention, separate windows (or sections) on the same touchscreen can allow a medic to drag and drop clinical information from the monitor defibrillator to a software application or vice versa with one simple hand gesture, for example. The concept of separate windows includes not only open applications, but also icons on a desktop, system tray, or menu bar, file management, etc. For example, dragging and dropping a piece of information from one application onto an icon might initiate file saving, emailing, or wireless communications to remote locations.

Figure 1:
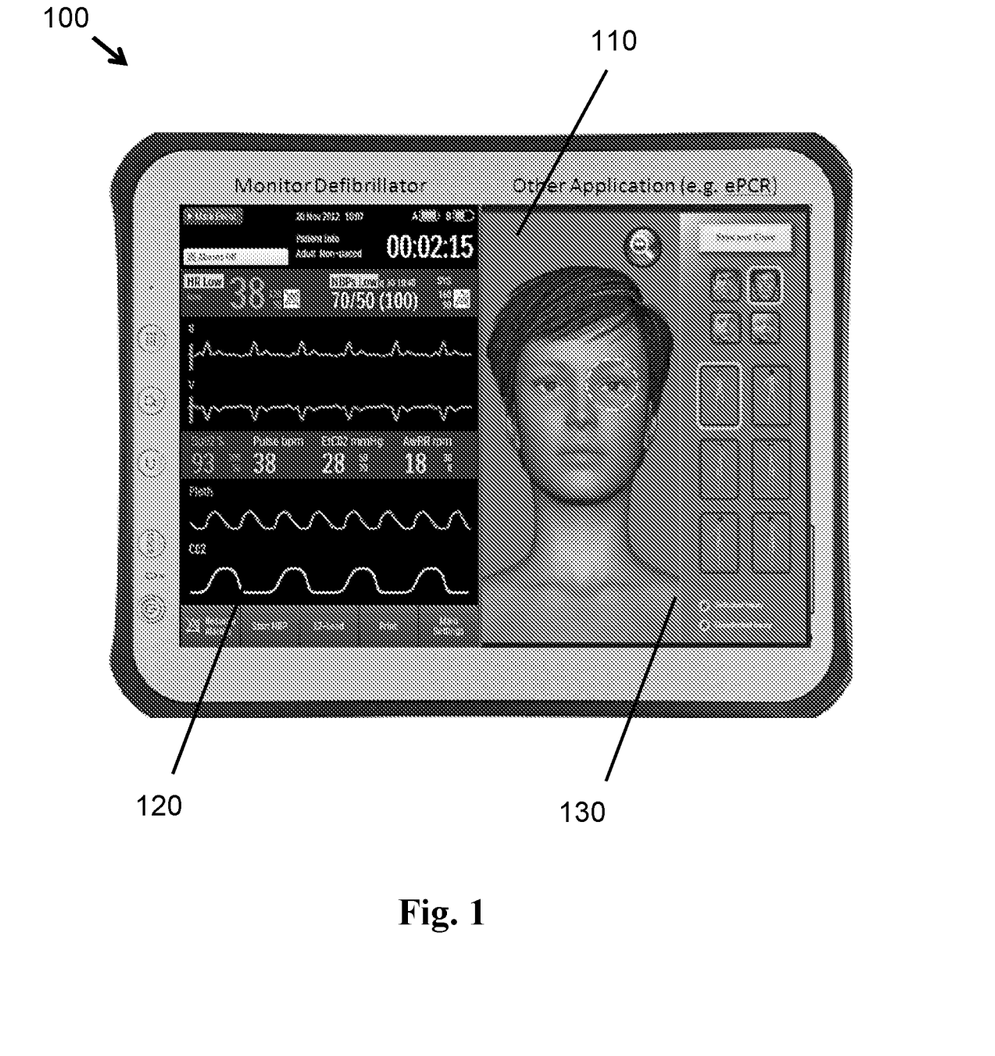
FIG. 1 illustrates an exemplary embodiment of a monitor defibrillator display in accordance with the present invention that includes two user interface windows on the same touchscreen.

For example, FIG. 1 illustrates an exemplary embodiment of a monitor defibrillator display 100 in accordance with the present invention that includes two user interface windows 120, 130 on the same touchscreen 110.

As shown in FIG. 1, the user interface (U/I) window on the left 120 represents the monitor defibrillator, and the U/I window on the right 130 represents an ePCR application. The example above illustrates two windows but the same concept would apply to more than two U/I windows, within practical limits of size and visibility, especially in embodiments when all windows are to be tiled so as to be completely visible at the same time. However, accordingly to certain exemplary embodiments of the present invention, it is possible to have a larger number of windows where not all windows are necessarily entirely visible at the same time, but rather the less important windows could be toggled with the windows displaying critical data being always visible. This toggling could be manually initiated or automatically executed (e.g., a window displaying information that changed or that is awaiting input can automatically toggle or pop-up in front). For example, while one window would always be dedicated to the functions of the monitor defibrillator (e.g., monitoring and therapy), the other window(s) could be allocated to a variety of EMS software applications including but not limited to ePCR.

The touchscreen can be integrated into a primary unit of a monitor defibrillator or a remote tablet for hand held convenience.

Figure 2:
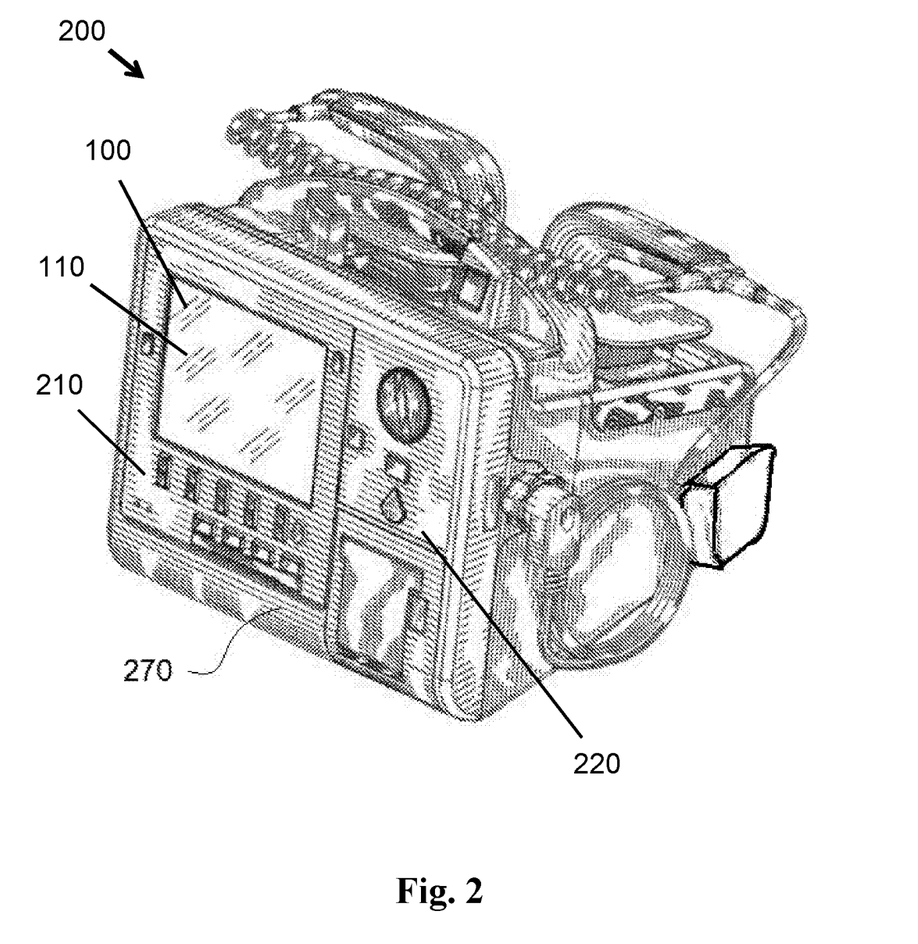
FIG. 2 illustrates an exemplary embodiment of a primary unit of a monitor defibrillator into which a touchscreen in accordance with the present invention is integrated.

FIG. 2 illustrates an exemplary embodiment of a primary unit of a monitor defibrillator 200 into which a touchscreen in accordance with the present invention is integrated. A unitary housing 270 contains display 100 including touchscreen 110. Unitary housing 200 also contains a patient monitoring unit 210 including a patient monitoring circuit, and a therapy unit 220 including a defibrillation therapy circuit. Unitary housing 270 can also contain a clinical processor, memory, a firewall circuit, and a communications interface.

Practical considerations include sufficient size for multiple windows (e.g. 10.1 inch diagonal) and adequate display resolution (1024×768) to render waveforms and monitoring parameters.

To run independent or third-party applications in the additional touchscreen window(s), the monitor defibrillator system can include a standard operating system (e.g. Microsoft Windows®) and isolation between clinical functions and independent or third-party applications. For example, U.S. Provisional Patent Application No. 61/745, 833, filed Dec. 26, 2012, entitled "Monitor Defibrillator Telemedicine Server", the entire disclosure of which is hereby incorporated herein by reference, discloses and describes exemplary embodiments of safety-critical therapy/monitoring functions running safely alongside non-safety-critical ePCR functions. More particularly, the referenced provisional patent application teaches a patient monitoring circuit and a defibrillator therapy circuit may be separate physical processors that operate independently from each other and are separately coupled to a clinical processor, which collects data from both circuits. In an exemplary embodiment of the present disclosure in accordance with the same operating principle of the referenced provisional, a monitor defibrillator and an application processor are embodied as separate physical processors that operate independently of each other and are separately coupled to a display, which simultaneously display two separate independently operated graphical user interfaces, one of the interfaces corresponding to the monitor defibrillator and the other interface corresponding to the application processor. Wireless connectivity can also be implemented, especially in exemplary embodiments of the present invention needing to have the capability to run (EMS) applications that are hosted remotely or cloud based, e.g., with only a thin client running for the user interface window.

Referring back to FIG. 1 and the exemplary embodiment of the present invention illustrated therein, the monitor defibrillator window (120) can be configured to be always active and visible so that the patient vital signs and monitoring parameters are always in the medic's field of view. EMS operators would have no opportunity or means to run other applications in the monitor defibrillator window. Alternatively, the other window (130) can be allocated to independent or third-party software and configured to run one or more EMS applications, e.g., depending on the preference and needs of the EMS agency and/or situation. For example, if desired, the entire display (100) and/or touch screen (110) can be used as the monitor defibrillator window; e.g., a simple touch or swipe action may "hide" the other window. This display functionality can be configured at the manufacturer's level, agency level (e.g., only by someone with configuration privileges) or in the filed by the user, for example.

Further, according to exemplary embodiments of the present invention, monitor defibrillator software can arbitrate data flow between the monitor defibrillator and applications running in other user interface window(s). For example, data such as the dispatch number, patient name, or medical history can flow from independent or third-party applications to the monitor defibrillator; whereas patient data including clinical monitoring parameters and vital signs can flow from the monitor defibrillator to independent or third-party applications. Moreover, the flow of information can be configured and controlled to be in compliance with applicable laws and regulations to protect patient health care information, including, but not limited to, being transmitted, utilized and/or stored anonymously as appropriate for providing EMS or other medical services while still being in compliance with such laws and regulations.

EMS medics can use appropriate touch gestures to transfer data from one user interface to another. For example, according to certain exemplary embodiments of the present invention, touching the non-invasive blood pressure (NIBP) result on the monitor defibrillator U/I window and subsequently sliding the fingertip to the other window will transfer the result to the third-party or other (operating system, remote location, etc.) application. Conversely, touching the patient name (or number or alias) in the third-party application window and subsequently sliding the fingertip to the monitor defibrillator window will transfer the name to the monitor defibrillator.

Exemplary embodiments of a monitor defibrillator according to the present invention can also be configured to automatically populate data fields from one U/I window to the other pending system integration of EMS agency workflow with independent or third-party applications.

Figure 3:
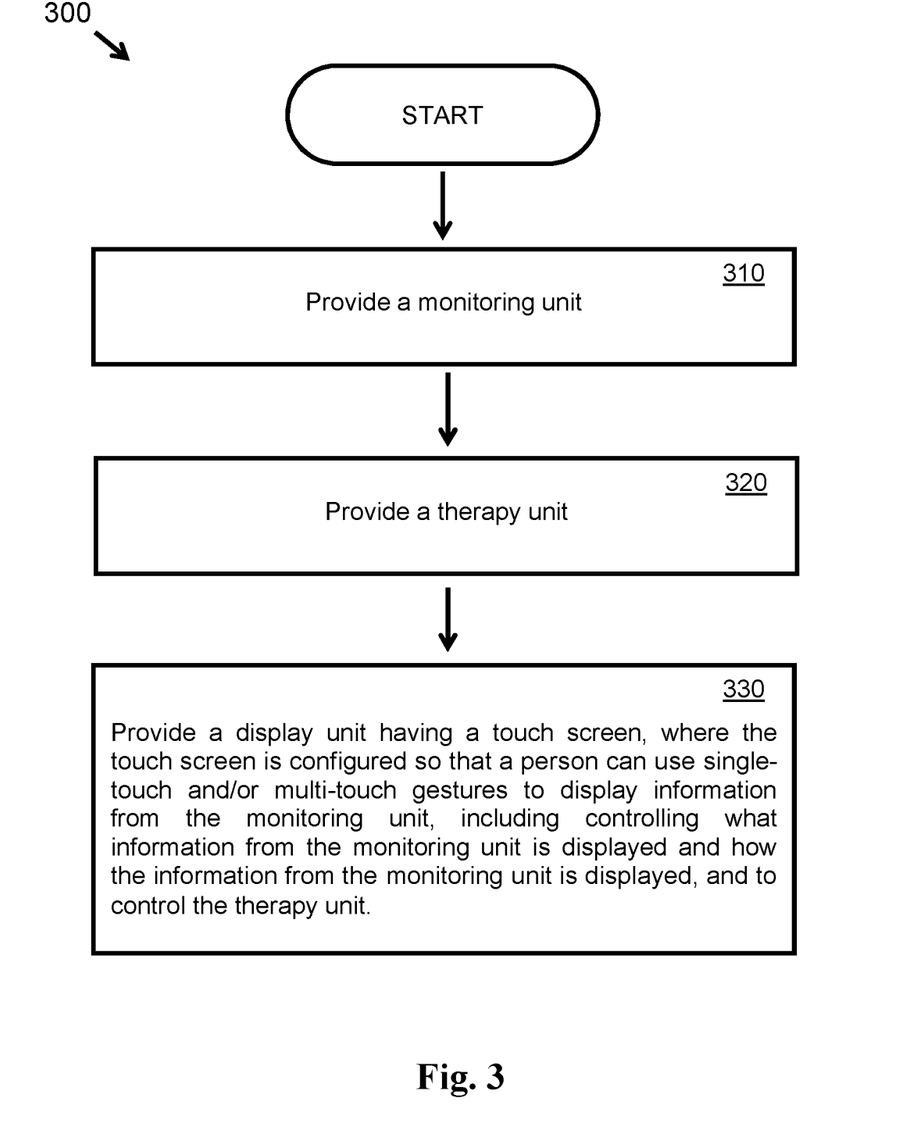
FIG. 3 illustrates a flow diagram of an exemplary method of manufacturing a device in accordance with the present invention.

FIG. 3 illustrates a flow diagram 300 of an exemplary method of manufacturing a device in accordance with the present invention. For example, a monitoring unit, such as monitoring unit 210, is provided at providing a monitoring unit step 310. A therapy unit, such as therapy unit 220, is provided at providing a therapy unit step 320. A display unit, such as display 100, having a touch screen is provided in providing a display unit having a touch screen step 330, where the touch screen is configured so that a person can use single-touch and/or multi-touch gestures to display information from the monitoring unit, including controlling what information from the monitoring unit is displayed and how the information from the monitoring unit is displayed, and to control the therapy unit. The touch screen can be touchscreen 110 disclosed and described herein, for example.

Some exemplary embodiments of the method can also include configuring the monitoring unit to be capable of monitor a person's electrocardiogram (ECG) and/or configuring the therapy unit to be capable of administering an electric shock.

Figure 4:
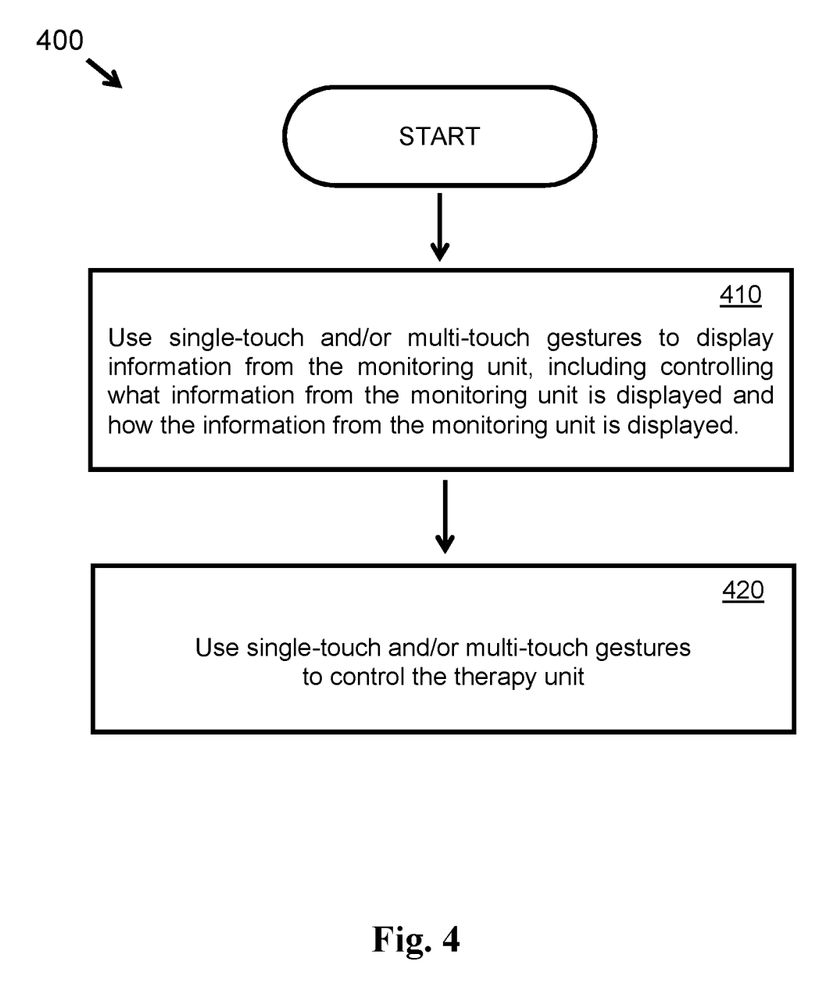
FIG. 4 illustrates a flow diagram of an exemplary method of using a device in accordance with the present invention.

FIG. 4 illustrates a flow diagram 400 of an exemplary method of using a device in accordance with the present invention. For example, at step 410, an operator can use single-touch and/or multi-touch gestures to display information from the monitoring unit, including controlling what information from the monitoring unit is displayed and how the information from the monitoring unit is displayed. At step 420, the operator can use single-touch and/or multi-touch gestures to control the therapy unit. Some exemplary embodiments of the method can also include monitoring a person's electrocardiogram (ECG) displayed on the display unit and administering an electric shock via the therapy unit based on information displayed on the display unit.

While this invention has been described with respect to monitors defibrillators, such as in-hospital monitor/defibrillators (e.g., used by hospital personnel) and/or pre-hospital monitor/defibrillators (e.g., used by EMS personnel), one having ordinary skill in the art shall appreciate in view of the teaching provided herein that exemplary embodiments of the present invention can be implemented in other medical devices, including, but not limited to, patient monitors (e.g., ECG monitors), automatic external defibrillators (AEDs) and/or other defibrillators. Indeed, exemplary embodiments of the present invention implemented in these other types of products are specifically contemplated and considered to be within the scope of the present invention.

Further, as one having ordinary skill in the art will appreciate in view of the teachings provided herein, features, elements, components, etc. described in the present disclosure/specification and/or depicted in the appended Figures may be implemented in various combinations of hardware and software, and provide functions which may be combined in a single element or multiple elements. For example, the functions of the various features, elements, components, etc. shown/illustrated/depicted in the Figure can be provided through the use of dedicated hardware as well as hardware capable of executing software in association with appropriate software. When provided by a processor, the functions can be provided by a single dedicated processor, by a single shared processor, or by a plurality of individual processors, some of which can be shared and/or multiplexed. Moreover, explicit use of the term "processor" or "controller" should not be construed to refer exclusively to hardware capable of executing software, and can implicitly include, without limitation, digital signal processor ("DSP") hardware, memory (e.g., read only memory ("ROM") for storing software, random access memory ("RAM"), non-volatile storage, etc.) and virtually any means and/or machine (including hardware, software, firmware, combinations thereof, etc.) which is capable of (and/or configurable) to perform and/or control a process.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (e.g., any elements developed that can perform the same or substantially similar function, regardless of structure). Thus, for example, it will be appreciated by one having ordinary skill in the art in view of the teachings provided herein that any block diagrams presented herein can represent conceptual views of illustrative system components and/or circuitry embodying the principles of the invention. Similarly, one having ordinary skill in the art should appreciate in view of the teachings provided herein that any flow charts, flow diagrams and the like can represent various processes which can be substantially represented in computer readable storage media and so executed by a computer, processor or other device with processing capabilities, whether or not such computer or processor is explicitly shown.

Furthermore, exemplary embodiments of the present invention can take the form of a computer program product accessible from a computer-usable and/or computer-readable storage medium providing program code and/or instructions for use by or in connection with, e.g., a computer or any instruction execution system. In accordance with the present disclosure, a computer-usable or computer readable storage medium can be any apparatus that can, e.g., include, store, communicate, propagate or transport the program for use by or in connection with the instruction execution system, apparatus or device. Such exemplary medium can be, e.g., an electronic, magnetic, optical, electromagnetic, infrared or semiconductor system (or apparatus or device) or a propagation medium. Examples of a computer-readable medium include, e.g., a semiconductor or solid state memory, magnetic tape, a removable computer diskette, a random access memory (RAM), a read-only memory (ROM), flash (drive), a rigid magnetic disk and an optical disk. Current examples of optical disks include compact disk—read only memory (CD-ROM), compact disk—read/write (CD-R/W) and DVD. Further, it should be understood that any new computer-readable medium which may hereafter be developed should also be considered as computer-readable medium as may be used or referred to in accordance with exemplary embodiments of the present invention and disclosure.

Having described preferred and exemplary embodiments for a monitor defibrillator with a touch screen user interface for ECG review and therapy, and of a monitor defibrillator having a touch screen with additional user interface window (s), (which embodiments are intended to be illustrative and not limiting), it is noted that modifications and variations can be made by persons skilled in the art in light of the teachings provided herein, including the appended Figure(s) and claims. It is therefore to be understood that changes can be made in/to the preferred and exemplary embodiments of the present disclosure which are within the scope of the embodiments disclosed herein.

Moreover, it is contemplated that corresponding and/or related systems incorporating and/or implementing the device or such as may be used/implemented in a device in accordance with the present disclosure are also contemplated and considered to be within the scope of the present invention. Further, corresponding and/or related method for manufacturing and/or using a device and/or system in accordance with the present disclosure are also contemplated and considered to be within the scope of the present invention.

What is claimed is:
1. A medical device, comprising:
a monitor defibrillator configured to generate output signals conveying information related to a person's electrocardiogram (ECG) and further configured to administer a therapy based on the information in the output signals;
an application processor physically separated from the monitor defibrillator and including one or more non-transitory software applications configured to collect and manage information related to the person; and
a display separately coupled to the monitor defibrillator and the application processor, wherein the display is configured to simultaneously display two separate independently operated graphical user interfaces,
wherein a first graphical user interface of the two separate independently operated graphical user interfaces has a monitor defibrillator window configured to display information related to a control of an operation of the monitor defibrillator,
wherein a second graphical user interface of the two separate independently operated graphical user interfaces has an application window configured to display the one or more non-transitory software applications configured to collect and manage information related to the person, and
wherein the display comprises a touch screen.
2. The medical device of claim 1,
wherein the display is configured to display the ECG in the monitor defibrillator window, and
wherein, responsive to receiving one or more touch inputs by a user, the display is configured to enable the user to:

scroll back and forth though previously displayed segments of the ECG, and select two or more separate segments of the ECG to be displayed together simultaneously in the monitor defibrillator window.

3. The medical device of claim 2, wherein the display is further configured to enable the user to zoom in and zoom out the displayed ECG by touching the touch screen.

4. The medical device of claim 2, wherein the segments are separated by intervening segments of the ECG, and wherein the display is further configured to enable the user to hide the intervening segments from being viewed on the display.

5. The medical device of claim 1, wherein the touch screen is configured to be used by a user via at least one of single-touch controls or multi-touch controls.

6. The medical device of claim 1, wherein the monitor defibrillator being configured to administer the therapy based on the information in the output signals includes the monitor defibrillator configured to administer an electric shock.

7. The medical device of claim 6, wherein the monitor defibrillator being configured to generate output signals conveying information related to the person's electrocardiogram includes the monitor defibrillator configured to monitor a person's vital signs.

8. The medical device of claim 1, wherein responsive to a touch input indicating a dragging and a dropping of a piece of information from the application window to the monitor defibrillator window, the display is further configured to modify the contents of the monitor defibrillator window to include the piece of information; or responsive to a touch input indicating a dragging and a dropping of a piece of information from the monitor defibrillator window to the application window, the display is further configured to modify the contents of the application window to include the piece of information.

9. The medical device of claim 1, wherein the one or more non-transitory software applications includes an electronic patient care record (ePCR) application.

10. The medical device of claim 9, wherein the touch screen is configured to enable a user to at least one of set monitoring parameters, initiate the administration of an electric shock, navigate menus, enter information in the cPCR, or at least one of retrieve or transmit information to at least one of a remote computer or cloud.

11. A method of manufacturing a medical device including a monitor defibrillator, an application processor and a display, the method comprising the steps of:

providing the monitor defibrillator configured to generate output signals conveying information related to a person's electrocardiogram (ECG) and further configured to administer a therapy based on the information in the output signals;

providing the application processor physically separated from the monitor defibrillator and including one or more non-transitory software applications configured to collect and manage information related to the person; and providing the display separately coupled to the monitor defibrillator and the application processor to simultaneously display two separate independently operated graphical user interfaces, wherein a first graphical user interface of the two separate independently operated graphical user interfaces has a monitor defibrillator window configured to display information related to a control of an operation of the monitor defibrillator, wherein a second graphical user interface of the two separate independently operated graphical user interfaces has an application window configured to display the one or more non-transitory software applications configured to collect and manage information related to the person, and wherein the display includes a touch screen configured to enable a user to utilize at least one of single-touch or multi-touch gestures to display information from the monitor defibrillator, including controlling what information from the monitor defibrillator is displayed and how the information from the monitor defibrillator is displayed and to control an administration of the therapy by the monitor defibrillator.

12. The method of claim 11, wherein the monitor defibrillator being configured to administer the therapy based on the information in the output signals includes the monitor defibrillator configured to administer an electric shock.

13. The method of claim 11, wherein responsive to a touch input indicating a dragging and a dropping of a piece of information from the application window to the monitor defibrillator window, the display is further configured to modify the contents of the monitor defibrillator window to include the piece of information; or responsive to a touch input indicating a dragging and a dropping of a piece of information from the monitor defibrillator window to the application window, the display is further configured to modify the contents of the application window to include the piece of information.

14. A method of using a medical device comprising a monitor defibrillator, an application processor, and a display unit having a touch screen, the method comprising the steps of:

generating, with the monitor defibrillator, output signals conveying information related to a person's electrocardiogram (ECG);

collecting and managing, with the application processor being physically separated from the monitor defibrillator, information related to the person;

simultaneously displaying, with the display unit being separately coupled to the monitor defibrillator and the application processor, two separate independently operated user interfaces, wherein a first graphical user interface of the two separate independently operated user interfaces has a monitor defibrillator window displaying information related to the ECG and to control an administration of a therapy by the monitor defibrillator, and wherein a second graphical user interface of the two separate independently operated user interfaces has an application window displaying the one or more non-transitory software applications configured to collect and manage information related to the person;

using at least one of single-touch or multi-touch gestures to display information from the monitor defibrillator, including controlling what information from the monitor defibrillator is displayed and how the information from the monitor defibrillator is displayed; and using at least one of single-touch or multi-touch gestures to control an administration of the therapy by the monitor defibrillator.

15. The method of claim 14, further comprising:
administering an electric shock, with the monitor defibrillator, based on information displayed on the display unit.

16. The method of claim 14, further comprising:
monitoring a person's vital signs with the monitor defibrillator.

17. The method of claim 14, further comprising:
using a touch input indicating a dragging and a dropping of a piece of information from the application window to the monitor defibrillator window to modify the contents of the monitor defibrillator window to include the piece of information; or
using a touch input indicating a dragging and a dropping of a piece of information from the monitor defibrillator window to the application window to modify the contents of the application window to include the piece of information.

18. A medical device comprising:
a monitor defibrillator;
an application processor physically separated from the monitor defibrillator and including one or more non-transitory software applications configured to collect and manage information related to the person;
a touch screen display separately coupled to the monitor defibrillator and the application processor; and
a computer system programmed by computer-readable instructions that, when executed, cause the medical device to:
generate, with the monitor defibrillator, output signals conveying information related to a person's electrocardiogram (ECG);
administer, with the monitor defibrillator, a therapy based on the information in the output signals;
collect and manage, application processor, with the information related to the person;
simultaneously display, with the touch screen display, two separate independently operated graphical user interfaces,
wherein a first graphical user interface of the two separate independently operated graphical user interfaces has a monitor defibrillator window configured to display information related to a control an operation of the monitor defibrillator,
wherein a second graphical user interface of the two separate independently operated graphical user interfaces has an application window configured to display the one or more non-transitory software applications configured to collect and manage information related to the person; and
responsive to receiving one or more touch inputs by a user, selectively toggle the second graphical user interface between visible and hidden.

\* \* \* \* \*